United States Patent [19]

Zachry

[11] Patent Number: 4,889,230
[45] Date of Patent: Dec. 26, 1989

[54] PACKAGE OF STRUNG MEDICAL SPONGES

[75] Inventor: Kathy W. Zachry, Kingston, Tenn.

[73] Assignee: DeRoyal Industries, Powell, Tenn.

[21] Appl. No.: 312,695

[22] Filed: Feb. 17, 1989

[51] Int. Cl.⁴ .............................................. B65D 73/00
[52] U.S. Cl. ................................... 206/362; 206/370; 206/440
[58] Field of Search ...................... 206/361, 362, 362.4, 206/363, 370, 438–440, 63.3

[56] References Cited

U.S. PATENT DOCUMENTS

| 822,060 | 5/1906 | Lawler. | |
|---|---|---|---|
| 3,630,202 | 12/1971 | Small | 128/296 |
| 3,948,390 | 4/1976 | Ferreri | 206/370 |
| 4,361,231 | 11/1982 | Patience | 206/362 |
| 4,415,089 | 11/1983 | Ruffa | 206/370 |
| 4,429,789 | 2/1984 | Puckett, Jr. | 206/370 |
| 4,478,332 | 10/1984 | Wiestmiller | 206/361 |
| 4,494,653 | 1/1985 | Praderio | 206/370 |
| 4,637,513 | 1/1987 | Eldridge, Jr. | 206/363 |
| 4,793,483 | 12/1988 | Holmes | 206/363 |
| 4,832,198 | 5/1989 | Alikhan | 206/362 |

*Primary Examiner*—Jimmy G. Foster
*Attorney, Agent, or Firm*—Luedeka, Hodges & Neely

[57] ABSTRACT

A package of strung medical sponges, particularly neurosurgical sponges comprising a plurality of sponges releasably held on a planar member such as a card which is self-supporting and suitable for grasping in one's hand. The strings of the sponges are threaded upon the card in a manner that permits the ready removal of the sponges one by one and which captures the tails of the strings to provided a neat and efficient package.

11 Claims, 2 Drawing Sheets

PACKAGE OF STRUNG MEDICAL SPONGES

FIELD OF THE INVENTION

This invention relates to the packaging of surgical sponges for presentation in the course of surgery, and particularly is directed to the packaging of strung medical sponges of the neurosurgical class.

BACKGROUND OF THE INVENTION

Medical sponges, and in particularly neurological sponges, commonly comprise a fibrous web, the fibers of which may be cotton, rayon, polyester or other synthetic or a combination of these. The fibers are bonded one to another by mechanical and/or chemical bonds, either with or without bonding additives. Neurological sponges, generally are of two types, strung and unstrung. In the strung sponges the absorbent web commonly is relatively small, ranging from about ¼ inch square upwards. Most such sponges are less than about 3 inches in length and about 3 inches wide. The webs commonly are of about 1/32 inch thick. The strung sponges have attached thereto one or two strings, commonly a textile thread having one of its ends anchored to the web and the remainder of the string extending from the web to serve as a locator element. The unstrung sponges most often are larger than the strung sponges, ranging up to 6 inches in length and 3.5 inches in width. These sponges have no depending string attached thereto.

Neurological sponges are employed for absorbing blood and body fluids, but most frequently are saturated with saline or other solution and used to protect tissue or applied to the tip of a suction device for protecting the tissue when suction is applied.

In the course of a surgical procedure, the medical sponges are sterilized and supplied to the operating room table in units of 10 and are carefully counted after use. Because absorbent sponges very closely resemble tissue when the sponge is soaked with blood, it is at times difficult to distinguish the small blood-soaked sponge from the surrounding body tissue. Thus, it is common practice to attach to the sponge a locator string, commonly about 12 inches in length, of a textile material, for example, such string being kept at all times outside the surgical incision so that the presence of the sponge may be readily noted through observing the string. These sponges further are provided with a separate and distinct x-ray opaque element fixed to the sponge in a manner as prevents its dislodgement. In the event the count of the sponges following the surgery indicates that one or more of the sponges is missing and a search of the operating room fails to locate the missing sponge, while the patient is still in the operating room, a portable x-ray unit may be brought in and the surgical site x-rayed in an attempt to determine whether the sponge has been left inside the patient.

One of the major problems in the prior art packaging of medical sponges, particularly neurosurgical sponges, has been the ability to present the sponges individually. The problem of presenting these sponges is compounded by the presence of the long locator strings that are attached to the relatively small pads. Heretofore it has been proposed to mount the small sponges on a card with a string from the sponge passing through a slit, thence along one face of the card to engage one or more slits or slots until substantially the entire length of the string has been "wound" onto the card. These prior art packages have been difficult to grasp in the user's hand while attempting to remove one of the sponges, either the pad portion of the sponge or the string being disposed on the card in a position such that when the user grasps the card, the fingers of the hand contact either the string or the sponge thereby presenting opportunity for compromising the sterility of the sponge. Further, the slits or slots provided in the prior art cards are of a nature and/or location on the card that develops substantial and inordinate friction between the string and the card as the string is withdrawn through the slit. This friction may result in disengagement between the sponge and the string thereby rendering the sponge non-usable. Even though the friction may not be so great as to cause the pad to break away from its string, the force required between the pad and forceps in withdrawing the string from the slits is sufficiently great to dislodge fibers of the pad or even to tear the pad. Still further, the withdrawal of the strings from the slits or slots in the prior art cards is further compounded where the angle of direction change of the string as the string is wound onto the card is substantially acute, thereby increasing the friction between the string and the slit or slot as the string is pulled from the packaging. A further problem with the prior art devices is that the tail ends of the strings of the several sponges in the package are not anchored and tend to become entangled one with another and/or become entangled with other objects employed in the surgery; such as, forceps, retractors, etc.

In my copending application entitled SURGICAL SPONGE, there is disclosed a novel locator string for neurological sponges which application is incorporated herein by reference. My novel locator string comprises a plurality, e.g. 20 or more, monofilaments bundled together and helically wrapped with a yarn. This locator string is particularly sensitive to the friction encountered when withdrawing the string from the slits or slots of the prior art sponge packaging in that such friction can fray my new locator string under certain conditions. Further, my new locator string is slightly greater in cross-sectional area than the prior art textile strings thereby making it more difficult to withdraw from the prior art packaging.

In the prior art it has also been suggested that several, e.g. ten, sponges be arranged in a stack in or on the packaging. This arrangement has resulted in unacceptable entanglement of the strings in the immediate vicinity of the sponge pads so that withdrawal of a single sponge is further complicated.

It is therefore an object of the present invention to provide a package of strung medical sponges in which the several sponges are mounted individually in the packaging for ready withdrawal at the time of their use. It is another object of the present invention to provide a package of medical sponges in which the friction between the string and packaging is minimized. It is another object to provide a package of strung medical sponges which is readily sterilizable with either steam, radiation, or ethylene oxide gas.

SUMMARY OF THE INVENTION

In accordance with the present invention there is provided a package of strung medical sponges comprising a plurality of such sponges releasably held on a planar member such as a relatively stiff, self-supporting card. In one embodiment the card is of rectangular geometry with one of its ends having defined therein openings that pass through the thickness of the card and which are of a geometry and size sufficient to receive therethrough one of the strings of a strung sponge. Preferably this opening includes a slit that extends from the opening and opens outwardly of a first end of the card. A string is passed through such opening and caused to overlie the second, i.e. reverse, surface of the card and extend to and be received in a slot that opens outwardly of the right hand edge of the card, as the card is held in one's hand with the first major surface of the card facing the viewer. This first slot is of a geometry and size that is substantially greater than the cumulative cross-sectional area of all strings of all sponges received on the card. The strings are then caused to overly the face of the card and pass diagonally thereacross to engage a second slot in the left hand edge side margin of the card. The second slot is generally like the first slot and substantially a mirror image thereof. The strings passing through the second slot are then caused to overlie the reverse surface of the card with the tail of the strings being captured in a capture zone defined by a flap that is provided on the bottom margin of the card. As viewed in the manner described hereinabove, such flap is adapted to be folded back upon the reverse surface of the card to define such capture zone. In a preferred embodiment, the flap is of a dimension sufficient that it covers at least the closed end of the second slot to aid in retaining the strings that pass through such slot. Further, the flap may be provided with means such as a tab which is receivable in a further slot through the thickness of the card such that when the tab is received in such further slot, the flap is maintained in its folded position, thereby retaining the tails of the several strings in the capture zone defined between the flap and the back surface of the card.

DETAILED DESCRIPTION OF THE INVENTION

Figure 1:
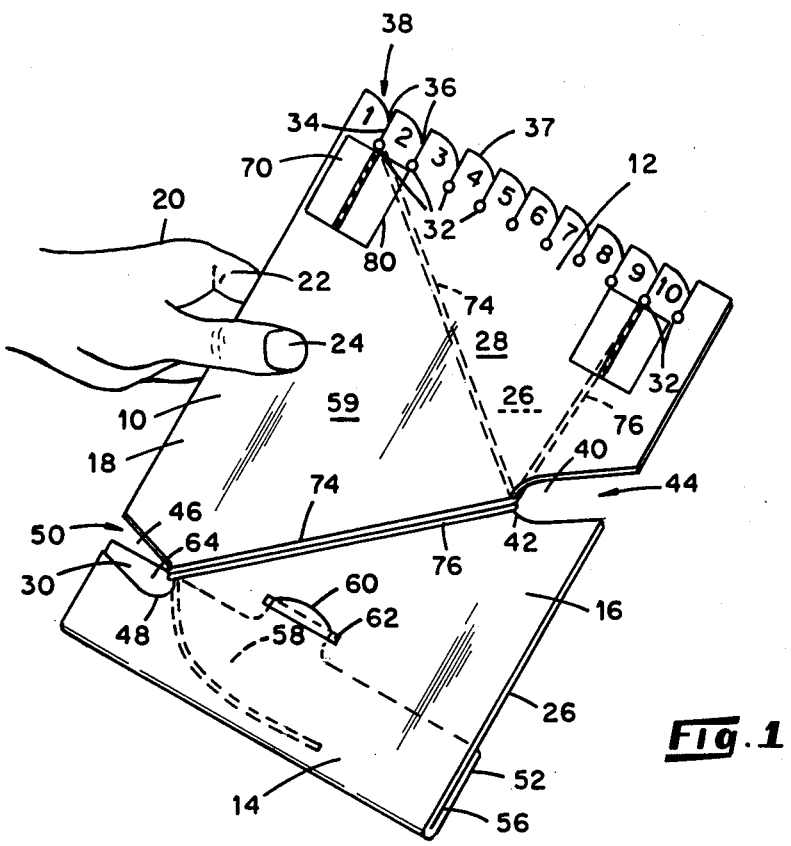
FIG. 1 is a representation of a package of strung medical sponges and depicting various features of the present invention.
Figure 2:
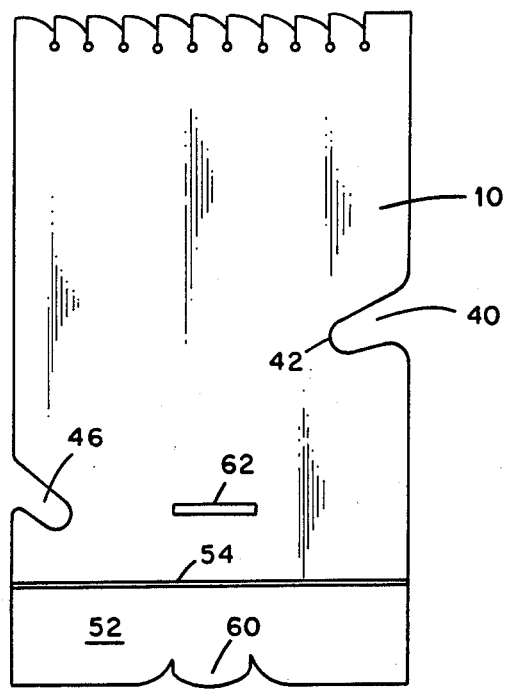
FIG. 2 is a plan view of one embodiment of a planar member suitable for use in the package of the present invention.
Figure 3:
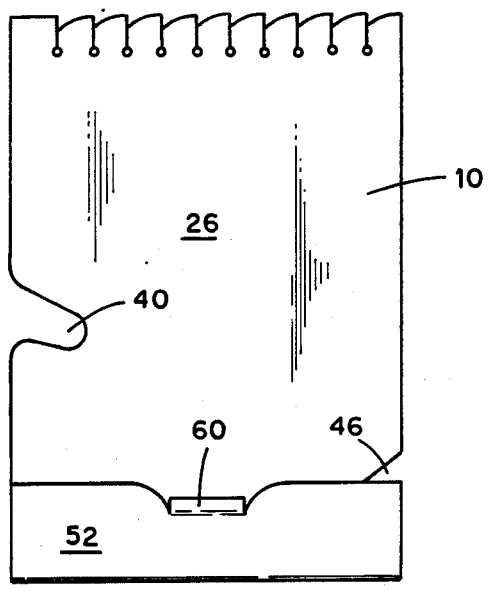
FIG. 3 is a plan view of the reverse side of the planar member of FIG. 2.

With specific reference to the figures, in FIG. 1 there is depicted one embodiment of a planar member 10 which in the preferred embodiment comprises a rectangular section of cardboard. The planar member 10 includes a first end margin 12, a second end margin 14, these end margins being connected by a first side margin 16 and a second side margin 18. The planar member, i.e., card 10, is sufficiently stiff as to be self-supporting and to be readily grasped in the hand 20 by placing the user's fingers on a first major surface 26 comprising the reverse surface of the card as depicted in FIG. 1, along the second side margin 18, and by positioning the thumb on a second major surface 28, i.e. face, of the planar member to thereby grasp the second side margin of the card between the thumb and fingers. It is important to note in this respect that the present package provides ample room for the thumb and fingers of the user without engaging the string or pad portion of the sponges held on the card as will appear more fully hereinafter. Furthermore, the card is of sufficient stiffness as to resist substantial bending when grasped between the thumb and fingers as described. The card preferably is of a cellulose fiber composition, but may be of other materials such as a polymeric material. In the latter instance, the material may be of a foam or cellular construction or of a relatively more solid construction.

In a preferred embodiment, the card has a width dimension between the first and second side margins of preferably about 5". The card has an end-to-end dimension of about 7" including an additional length of about 1¼" which defines a flap 30. The thickness of the cardboard is not critical but preferably is relatively thin, e.g., less than about 1/64".

The first end margin 12 of the card 10 is provided with a plurality of openings 32 that extend through the thickness of the card. Notably these openings are of a geometry, e.g. preferably round, and a size that is sufficient to permit the ready passage of a string 74 therethrough without substantial frictional drag upon the string. In the depicted embodiment each of the openings 32 includes means defining a slit 34 extending from the opening 32 and opening outwardly at 36 of the first end margin 12. Still further, in the preferred embodiment the opening 36 to the slit 34 is preferably flared as indicated by the arrow 38 to provide guidance for moving the string 74 through the slit 34 and into the opening 32. In the preferred embodiment, there are ten openings 32 aligned substantially parallel to and across the width dimension of the first end margin 12 adjacent its edge 37. Preferably each of the openings 32 has associated therewith a numerical indicia for identifying the respective openings.

As seen in FIG. 1, there is a first slot 40 defined along the first side margin 16 of the card 10 and extends from its closed end 42 to open outwardly at 44 of the first side margin 16. In the depicted and preferred embodiment, this slot is located approximately equidistant between the first and second end margins 12 and 14. This slot is substantially larger in size than is required to receive ten of the strings 74 therein, thereby affording free movement of the strings into and out of the slot and/or sliding movement of the strings through the slot in the direction of the thickness of the planar member 10. Further, the preferred positioning of the first slot 40 provides for clearance for larger sponges mounted on the face 28 of the card without interfering with the winding of their strings on the card as described herein.

A second slot 46 is defined in the second side margin 18 of the card 10 with its closed end 48 directed inwardly of the card 10 and opening outwardly as at 50 of the second side margin 18. Like slot 40, slot 46 is of a size and geometry that permits ready access and removal of at least ten of the strings 74 through the slot without undue friction between the slot and the string. As shown in FIG. 1, in the preferred embodiment, the second slot 46 is disposed approximately two-thirds of the distance between the first and second end margins 12 and 14 and nearer the second end margin 14 than the location of slot 40. In a preferred embodiment, the second slot is located a linear distance from the edge 37 of the first end margin 12 of about 3½ inches thereby providing adequate room to receive the user's fingers 22 and thumb 24 without contacting either the pad or the string. For similar reasons, and others the preferred width dimension is not less than about 2 inches.

The second end margin 14 of the planar member 10 includes a flap 52 which is foldable along a fold line 54 against the reverse surface 26 of the planar member 10 to define a capture zone 56 between the surface 26 and the flap 52 for the ends 58 of the strings 74 therebetween. In the depicted embodiment, the flap includes a tab 60 which is adapted to be received within a third slot 62 which extends through the thickness of the planar member 10 for maintaining the flap in the folded position.

Notably, the flap 52 is of a dimension such that it includes a portion 30 which overlies the closed end 48 of the second slot 46 and serves to capture the string 74 between the surface 64 of the flap 52 and the surface 26 of the planar member 10 at the location where the string passes through the slot 46, thereby enhancing the retention of the string within the slot against inadvertent falling out of the string, while not materially impeding the withdrawal of the string as the sponge is withdrawn from the card.

A plurality of strung medical sponges 70 are mounted on the card 10, such sponges being disposed in overlying relationship to the surface (face) 28 of the planar member 10 in the region of the first end margin 12. Only two sponges 70 and 72 are depicted in FIG. 1 for purposes of clarity but it will be recognized that the package normally includes ten such strung sponges. Each of the sponges 70 and 72 includes a string member 74 and 76 respectively. For purposes of clarity of description only, the positioning of the sponge 70 on the card 10 will be described, it being understood that the remaining sponges are similarly mounted in the package. Specifically, and with reference to FIG. 1, the string 74 of the sponge 70 is passed through the slit 34 and into the opening 32 to position the pad 80 of the sponge 70 in overlying relationship to the surface 28 and in a location close to the opening 32. Preferably, the sponge is substantially in contact with the margin of the opening 32 to limit its ability to move about relative to the opening 32 and/or the surface 28. As shown, the string 74 is caused to overlie the reverse surface 26 of the planar member 10 in a substantially straight line between the opening 32 and the closed end 42 of the slot 40, and enter into the slot 40, thence passing through the thickness of the card 10 and extend in a substantially straight line in overlying relationship to the surface 28 to enter the slot 46 and cause the tail 58 of the string 74 to pass through the thickness of the card 10 and enter the capture zone 56 defined by the flap 52. Each of the other sponges and their respective strings are similarly threaded upon the card 10 with the respective tails of the strings being contained and captured within the capture zone 56 so that these tails do not hang loose from the card to engage or become entangled with external objects. Further, the capturing of the tails in the capture zone maintains the tails against entanglement one with another so that these strings can be readily withdrawn individually from the capture zone.

In use, a surgeon or assistant grasps the card 10, as in their left hand. A sponge 70 commonly is withdrawn from the package by grasping it with forceps or the like and pulling on the sponge in a direction substantially perpendicular to the surface 28. As the sponge is pulled away from the surface 28, its string 74 is pulled through the slot 46, the slot 40, and the opening 32. It will be recognized that the size of the opening 32 and the relatively large size of the slots 40 and 46 permit substantially uninhibited movement of the string through these openings. Further, it is noted that as the string is threaded through the several openings and/or slots, the angle of directional change of the string at no time is an acute angle, but such directional change is of a substantial angle, e.g. at least about 90° or greater. This is important in reducing the friction exerted between the string and the card 10 at the points of directional change, for example at the slots 40 and 46 in particular.

I claim:

1. A package of strung medical sponges comprising a plurality of said sponges releasably held on a planar member, said planar member being sufficiently stiff as to be self-supporting and having first and second major surfaces, first and second end margins and first and second side margins, said end and side margins defining the perimeter of said planar member, means defining a plurality of string receiving openings through the thickness of said planar member adjacent the first end margin thereof, means defining a first slot means opening outwardly of said first side margin of said planar member and spaced away from said first end margin, means defining a second slot means opening outwardly of said second side margin of said planar member and spaced away from said first end margin by a distance substantially greater than the spatial distance between said first slot means and said first end margin, foldable flap means defined along said second end margin and including a planar flap portion adapted to fold back upon said first major surface of said planar member in the region of said second end margin and define a capture zone for string ends therebetween, and means for retaining said flap portion in such folded position, said sponges being positioned adjacent said first end margin in generally overlying relationship to said second major surface of said planar member with their respective string being received in said string receiving openings and through the thickness of said planar member, thence extending in overlying relationship to said first surface of said planar member in the direction of said first slot means, thence being received in said first slot means to extend to said second surface of said planar member, thence extending in overlying relationship to said second surface of said planar member in the direction of said second slot means, thence being received in said second slot means to extend to said first surface of said planar member, thence extending in overlying relationship to said second surface of said planar member such that the unattached ends of said strings terminate in said capture zone defined between said flat means and said first surface of said planar member.

2. The package of claim 1 wherein said first slot means is located approximately equidistant between said first and second end margins.

3. The package of claim 1 wherein said flap portion of said flap means, when folded back against said first surface, overlies at least the closed end of said second slot means.

4. The package of claim 1 and including indicia associated with respective ones of said string-receiving openings.

5. The package of claim 1 wherein each of said string-receiving openings includes means defining a slit extending from such opening and opening outwardly of said first end margin of said planar member.

6. The package of claim 5 wherein each of said string-receiving openings is of a geometry and size greater than the cross-sectional area of a string such that such string is freely movable through such opening.

7. The package of claim 5 wherein each slit includes a flared open end at its most outward extremity.

8. The package of claim 1 and including tab means associated with said flap portion and means defining a third slot extending through the thickness of said planar member in position to receive said tab means when said flap portion is folded back against said first surface of said planar member.

9. The package of claim 1 wherein said second slot means is spaced from the outermost edge of said first end margin by a linear distance as measured substantially parallel to said second side margin of not less than about 3.5 inches.

10. The package of claim 1 wherein the minimum linear distance between the first and second side margins of said planar member in the region thereof between said first slot means and said first end margin is not less than about 2 inches.

11. The package of claim 1 wherein said planar member is generally rectangular.

* * * * *